(12) United States Patent
Castillejos

(10) Patent No.: US 8,157,759 B2
(45) Date of Patent: Apr. 17, 2012

(54) METHOD AND APPARATUS FOR FLUID DRAINAGE OF THE EYE

(75) Inventor: David Castillejos, San Diego, CA (US)

(73) Assignee: Ocumatrix, Inc., La Jolla, CA (US)

( * ) Notice: Subject to any disclaimer, the term of this patent is extended or adjusted under 35 U.S.C. 154(b) by 397 days.

(21) Appl. No.: 12/468,014

(22) Filed: May 18, 2009

(65) Prior Publication Data
US 2009/0287136 A1 Nov. 19, 2009

(51) Int. Cl.
*A61M 5/00* (2006.01)
(52) U.S. Cl. .................................. 604/8; 604/9
(58) Field of Classification Search ............... 604/8, 9
See application file for complete search history.

(56) References Cited

U.S. PATENT DOCUMENTS

| 4,643,716 | A  | * | 2/1987  | Drach ............................ 604/8 |
| 5,180,362 | A  | * | 1/1993  | Worst ............................ 604/8 |
| 6,736,791 | B1 | * | 5/2004  | Tu et al. ......................... 604/8 |
| 7,488,303 | B1 | * | 2/2009  | Haffner et al. ................ 604/8 |
| 2003/0236483 | A1 | * | 12/2003 | Ren ................................ 604/8 |
| 2004/0193095 | A1 | * | 9/2004  | Shadduck ..................... 604/8 |
| 2004/0193262 | A1 | * | 9/2004  | Shadduck .................. 623/4.1 |
| 2004/0254520 | A1 | * | 12/2004 | Porteous et al. ............... 604/8 |

* cited by examiner

*Primary Examiner* — Leslie Deak
(74) *Attorney, Agent, or Firm* — Donn K. Harms

(57) ABSTRACT

An implantable drain for the anterior chamber of the eye for venting fluid therefrom to relieve pressure. The device features a serpentine draining conduit having an aggregate length much longer than a liner conduit. The conduit is engaged within the sclera in a pocket formed under a scleral flap. The conduits may be interchanged with a shunt or other component communicating into the anterior chamber.

6 Claims, 5 Drawing Sheets

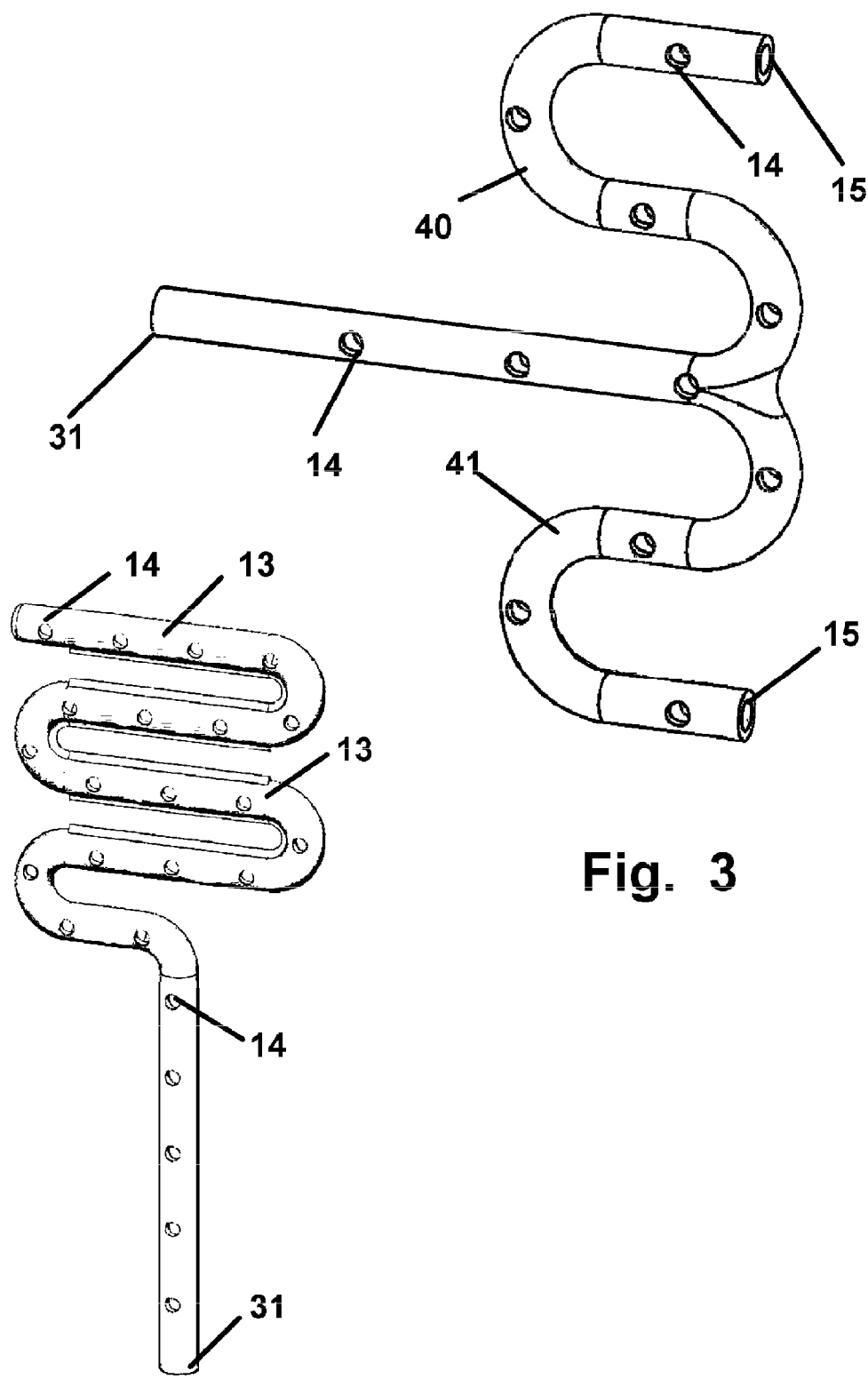

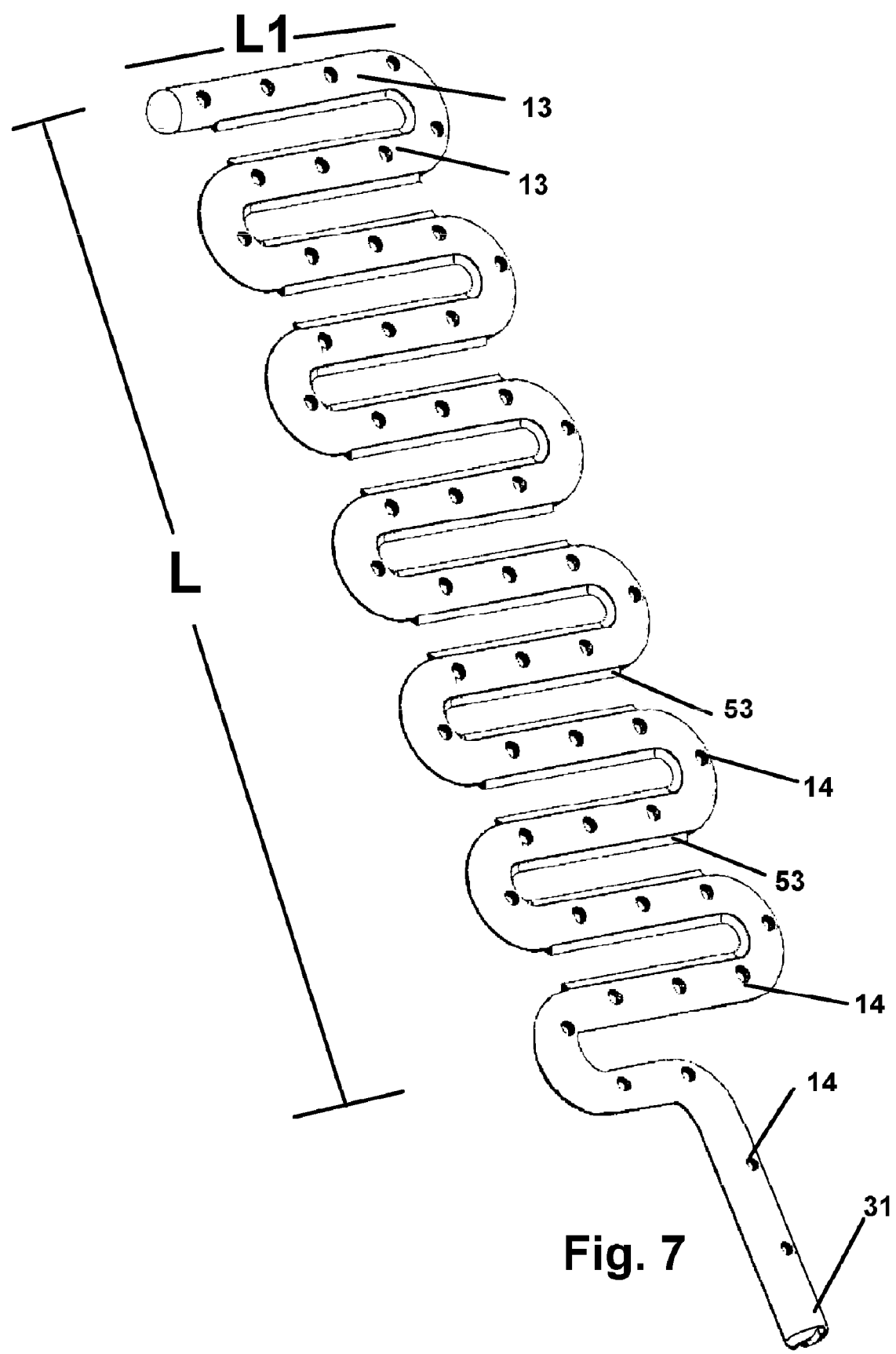

METHOD AND APPARATUS FOR FLUID DRAINAGE OF THE EYE

This application claims priority to U.S. Provisional Patent Application No. 61/054,080 filed on May 16, 2008 and which is incorporated herein in its entirety by reference.

BACKGROUND OF INVENTION

Field of Invention

The disclosed device relates to an implant for the eye. More particularly it relates to a drainage device which when placed in communication with the anterior chamber of the eye, provides a serpentine drainage conduit for fluid into the scleral layer of the eye.

Glaucoma is a disease of the eye which is caused by increased intraocular pressure (IOP) within the interior of the eye. This increased pressure results generally either from a malformation, or from a malfunction of the eye's drainage structures. Intraocular pressure beyond normal limits, if left untreated, will cause irreversible damage the optic nerve and retinal fibers. Such physical damage to the structures of the eye generally result in a progressive, permanent loss of vision. However, early detection of IOP with proper treatment can slow, or even halt the progression of the disease.

A general cause of high IOP and Glaucoma is the excess fluid accumulating in the anterior chamber. The eye constantly produces a clear aqueous fluid which fills the anterior chamber (the space between the cornea and iris). In a healthy eye, the aqueous fluid filters out of the anterior chamber through a complex drainage system.

When the drainage system goes wrong, Glaucoma can develop which is an eye disease wherein the patient gradually loses their sight. High IOP frequently accompanies Glaucoma and is believed to be one of the main causes of the nerve damage causing this vision loss.

Drugs are frequently used on cases where intraocular pressure slowly builds and they frequently work well to control it. In patients suffering a rapid rise in IOP or a long term rise that has reached a dangerous plateau, severe eye damage and permanent loss of sight can result.

Surgery has also been used more recently to treat intraocular pressure. Clinical investigators have noted in recent years that intraocular pressure is lowered following radial incisions in the anterior sclera, known as an anterior ciliary sclerotomy. Unfortunately, for patients undergoing such a procedure, the beneficial effects are frequently negated over a period of time following the procedure as the incisions heal and scar. Further, most such surgeries provide no means to adjust the ultimate drainage flow and the patient may suffer from too much, or too little flow after the surgery. Consequently the potential for eyesight loss arises as pressure again builds following the surgery.

As a result, there is a continuing need for a device and method for implantation, which will provide for a simple surgical procedure resulting in long lasting, customizable relief from high IOP. Such a treatment should provide for a simple component engagement to the anterior chamber. Such a device and method, because of the delicate nature of fluid production and fluid drainage in the eye affecting vision, should be customizable to the patient to allow both more, or less fluid flow and drainage from the anterior chamber. Further such a device and procedure should be easily performed and easily reversible in addition to being customizable for flow during and subsequent to the operation.

SUMMARY OF THE INVENTION

The above shortcomings of current and prior art are overcome by the herein disclosed method and apparatus providing a drainage means to the anterior chamber.

The device features a serpentine shaped conduit which allows for a maximizing of the aggregate length of the drainage conduit, even mounted in the small area the eye provides for such implants. A plurality of apertures communicate from the axial chamber running through the conduit to the exterior of the wall defining conduit, to thereby provide fluid drainage therefrom and from the communicating anterior chamber.

Communication between the conduit, and the anterior chamber may be provided by a first end adapted to engage the anterior chamber, or in a particularly preferred mode, by an engagement component such as a shunt. The shunt is adapted on a first end to pierce through the eye to the anterior chamber, and on a second end for sealed attachment of an engagement end of the drainage conduit. An internal passage communicates through the shunt or other engagement component from the first end to the second end. The first end may have a knife-edged portion for self-piercing of the eye, or may be implanted through an aperture or other incision formed by the surgeon to communicate with anterior chamber.

The second end of the shunt or other engagement component has a means for sealed engagement of the input aperture end of the elongated conduit. This may be a bulge, or a slip fitting, an aperture, or simply an adhesive joined engagement, or other engagements those skilled in the art will realize after reading this disclosure, which seals the axial cavity of the serpentine conduit, with the axial passage communicating through the engagement component into the anterior chamber.

The device is customizable to the patient in that the flow rate from the device, of fluid communicated from the anterior chamber, may be calculated and fine-tuned. This may be done by employing a serpentine conduit of differing total aggregate lengths, or having different diameter axial passages in the conduits, or by having more or less drainage holes, or by adjusting the size of the drainage holes, or by one or a combination of one or all of the above.

Thus, the device may be provided in kit form, where the surgeon chooses a shunt or other engagement component adapted to the patient's eye. Then, a properly dimensioned and configured serpentine conduit, adapted to provide the flow rate for exiting fluid from the anterior chamber that is determined optimum for the patient would be engaged to the shunt or engagement component. Changing the aperture sizes of the conduit, the aggregate length of the conduit, the interior axial cavity size of the conduit, one or in combination thereof will allow for the provision of an infinite number of conduits with an infinite number of flow rate variations.

Because the conduit may be removably engageable to the shunt, should a better flow rate for fluid be determined later on, a conduit with the correct aggregate length may be mounted to the shunt after removal of the first-employed conduit.

With the proper serpentine conduit chosen and having the proper aggregate length, the conduit is then mounted to the shunt or other engagement component which would be implanted to communicate on one end of its axial chamber with the anterior chamber. An attachment end of the serpentine conduit would be placed within a space formed by a scleral flap formed in the scleral layer of the eye by formation of the flap underneath which the conduit is placed. Engaged to the shunt, and so placed, the conduit will provide a drainage pathway having a total aggregate length well beyond its axial length thereby providing a major increase in drainage capability.

Once the shunt or engagement device is engaged to the anterior chamber and to a chosen conduit, fluid from the anterior chamber will drain to the scleral layer of the eye to maintain proper pressure in the anterior chamber and interior of the eye as well as maintaining proper fluid volume within the eye.

The conduit may be formed from tubular material, using molds or jigs, or from two planar components having ½ of the conduit formed therein as a recess. If planar material is employed, joining the planar components forms the serpentine conduit having an axial cavity running therethrough.

The implant is currently best made of a material that is inert when in contact with body tissue. Favored materials include one or a combination of materials from a group including hydroxiapartite, silicone, polymethylmethacrylate, acrylic, and tantalum.

Still further, while the conduit may have a shunt or engagement component formed of one end of the conduit, using a separate engageable shunt or component to communicate with the anterior chamber and with the conduit, allows the surgeon to change the conduit for length and for fluid flow characteristics to customize the fluid flow to the eye of the user. Thus, the device may be provided in kit form with a shunt or engagement component adapted to communicate on one end into the anterior chamber, and on a second end, with any of a plurality of different conduits having different fluid flor wate characteristics.

Accordingly, it is the object of this invention disclosed herein to provide a reliable method of surgery for the placement of implants in the sclera which provide maximum drainage from the interior of the eye and anterior chamber when operatively placed.

It is another object of this invention to provide an implant that is easily insertable form permanent engagement solely into the a pocket formed in the scleral layer of the eye during a surgical procedure.

It is still another object of this invention to provide such an implant that has a shunt or other engagement component adapted to communicate between the eye, and any number of differently configured conduits.

Yet another object of this invention is the provision of a method and apparatus above in a kit that provides a means to customize the flow rate of fluid exiting the anterior chamber through the conduit.

These and further objectives of this invention will be brought out in the following part of the specification, wherein detailed description is for the purpose of fully disclosing the invention without placing limitations thereon.

BRIEF DESCRIPTION OF THE DRAWING FIGURES

The accompanying drawings which are incorporated in and form a part of this specification illustrate embodiments of the disclosed device and together with the description, serve to explain the principles of the invention.

FIG. 3 depicts a mode of the serpentine conduit extending in two directions from a central engagement with a neck portion of the conduit.

FIG. 4 depicts a mode of the device employing a neck which engages or becomes a serpentine conduit at a second end.

FIG. 7 depicts a mode of the device showing the relationship of the axial length of the conduit, to the total aggregate length which may be achieved using a serpentine shape.

DETAILED DESCRIPTION OF THE PREFERRED EMBODIMENTS OF THE DISCLOSED DEVICE

Figure 1:
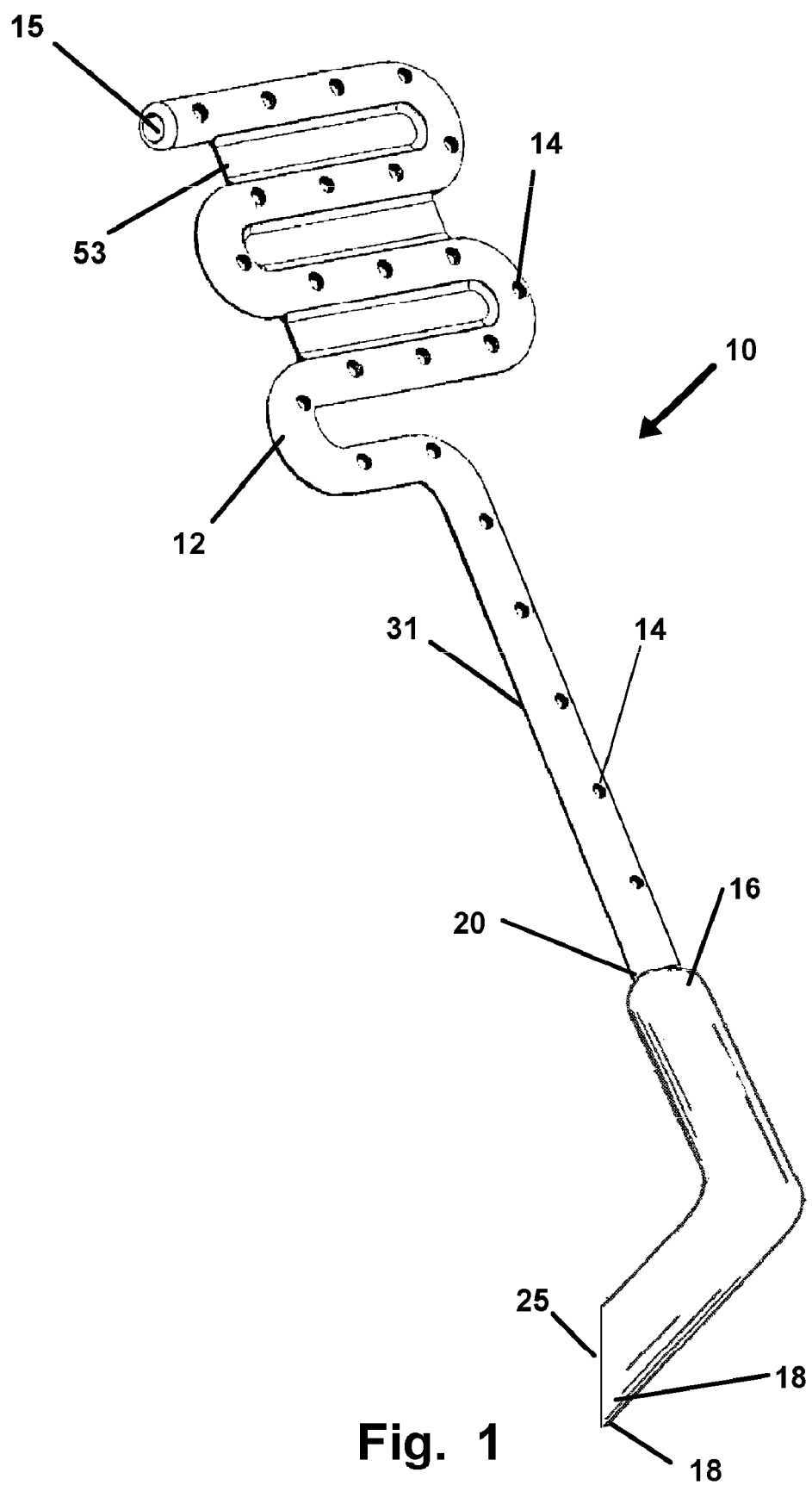
FIG. 1 depicts the serpentine shape of the preferred conduit which has drainage apertures communicating with an axial chamber and which is engageable in a sealed engagement to a shunt or engagement component.
Figure 2:
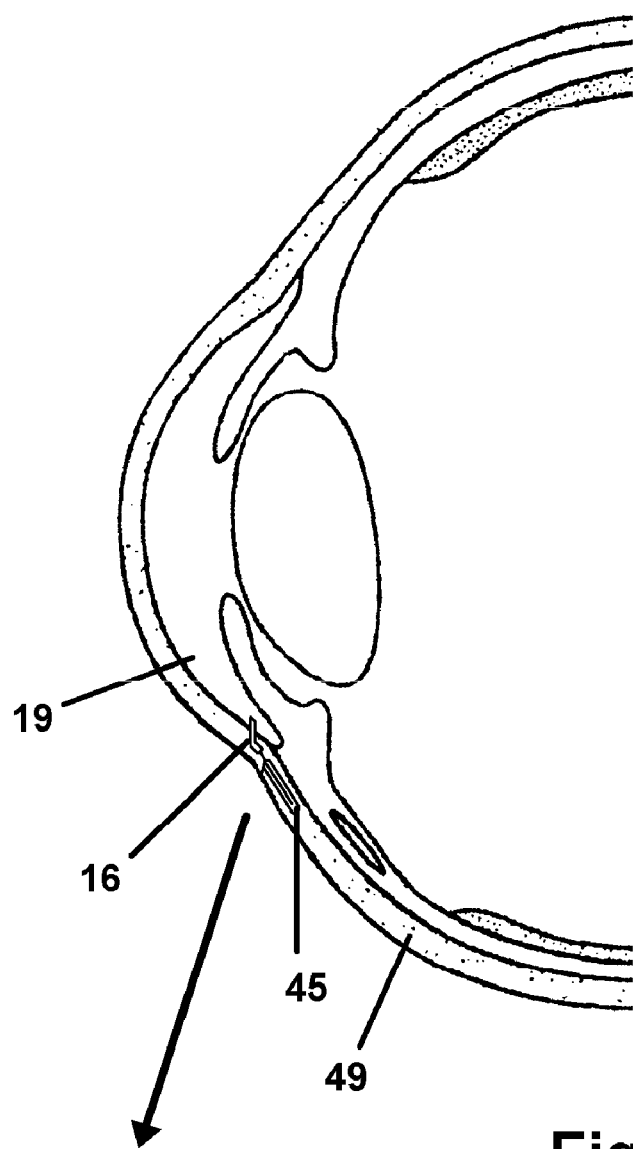
FIG. 2 shows the device engaged within an eye with the engagement component communicating with the anterior chamber and with the conduit housed in a pocket in the scleral layer of the eye.
Figure 2A:
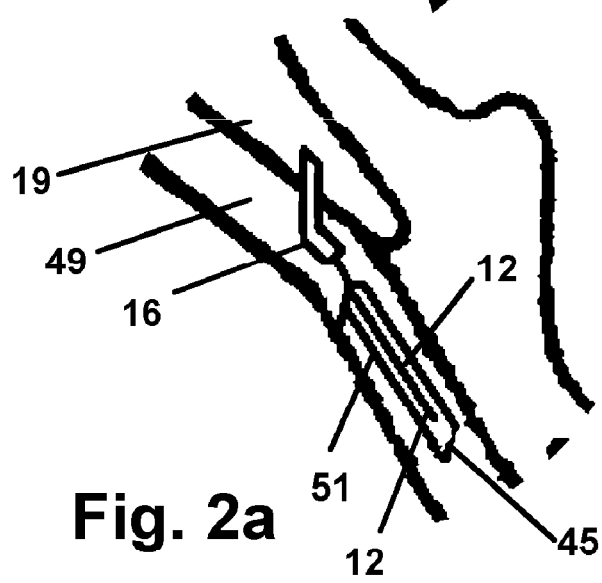
FIG. 2a is a blow-up of a portion of FIG. 2 showing the device engaged in a pocket in the sclera and communicating fluid from the anterior chamber through the engagement component and to the conduit.

Referring now to FIGS. 1-7, the various figures depict the preferred embodiments of the disclosed device 10, which employs a unique serpentine shaped conduit 12 which has a total aggregate length which is much larger than the axial length "L" shown in FIG. 7. The back and forth translations of the conduit 12 in FIGS. 1, 3-4, and specifically 7, for a distance L1 on each translation, will yield a total aggregate length at least three to four times the axial length "L". The total aggregate length may be adjusted by adding or subtracting translating sections 13, and by changing their length "L1". The serpentine conduit so formed thereby maximizes the lengths of the drainage conduit 12 available in the surface of the sclera to disperse fluid. The serpentine shape also lends itself to adjustment for flow and employment as a kit of different conduits having different total aggregate lengths.

In all modes of the device 10, a plurality of apertures 14, communicate from the interior axial passage 17 of the serpentine conduit 12, to the exterior of the conduit 12. The apertures thus provide fluid drainage at a defined rate depending on the size of the apertures 14, the size of the axial passage 17, and the aggregate length of the conduit 12 and total number of apertures 14 along that length. Means to change the fluid flow rate is provided by adjusting any one or a combination of the number and size of the apertures 14, the diameter of the axial passage 17 communicating with the apertures 14, and the aggregate length of the conduit 12.

Means for a fluid communication between the conduit 12, and the anterior chamber of the eye and the axial passage 17 and the apertures 14, is provided by a shunt or engagement component 16. The engagement component adapted on a first end 18 to pierce through the eye into the anterior chamber 19, and on a second end 20 for sealed permanent or removable engagement 23 to the wall of the conduit 12 defining the axial passage 17 which ultimately communicates with all of the apertures 14.

An internal passage 25 axially communicates through the engagement component 16 from the first end 18 to the second end 20. The first end 18 may have a knife-edged portion 29 for self-piercing of the eye tissue, or the engagement component may be otherwise surgically implanted through an aperture or incision formed by the surgeon to the anterior chamber 19.

The second end 20 of the engagement component 16 has a means for sealed engagement of the input end 21 and axial passage 17 of the elongated conduit 12 which extends to either the last aperture 14 along the conduit or a distal end aperture 15 if included. As noted, this may be a bulge in a slip fitting, an aperture, or simply an adhesive joined engagement that seals the axial passage 17 of the serpentine conduit 12, with the passage 25 communicating through the engagement component 16.

As noted, the device 10 is customizable to the patient in that the fluid flow rate may be calculated and fine-tuned. This may be done by employing a serpentine conduit 12 of differing aggregate lengths which are determined by the axial length L, plus the number of serpentine segments or sections 13 times the sections 13 length. By increasing or decreasing the curved portions 37 of the conduit 12 connection the sections 13, more or less sections 13 may be placed along the axial length L. Increasing the aggregate length with apertures 14 increases the fluid flow capability, in a much smaller length "L" than would be possible using a linear conduit 12.

Adjustment is also achievable by having different diameter axial passages 17 therein, or by having more or less drainage apertures 14, or by adjusting the size of the drainage apertures 14, or by combinations of one or all of the above. Thus a kit of differently configured conduits 12 for different flow rates can be assembled, with each member of the kit adapted to engage either a shunt or engagement component 16. Should the chosen fluid flow rate be of a volume too small or too large, the surgeon can easily change the engaged conduit 12 component by disengaging the conduit 12 component and engaging another with different fluid flow characteristics. Indicia or color coding can allow the surgeon to discern flow rates against a reference chart.

Changing the aperture 14 sizes, the number of apertures 14 along the aggregate length, the actual aggregate length of the conduit 12, the interior passage 17 size of the conduit, in one or in a combination, will allow for the provision of an infinite number of fluid flow rates from configured conduits 12 with an infinite number of flow rate variations.

Figure 5:
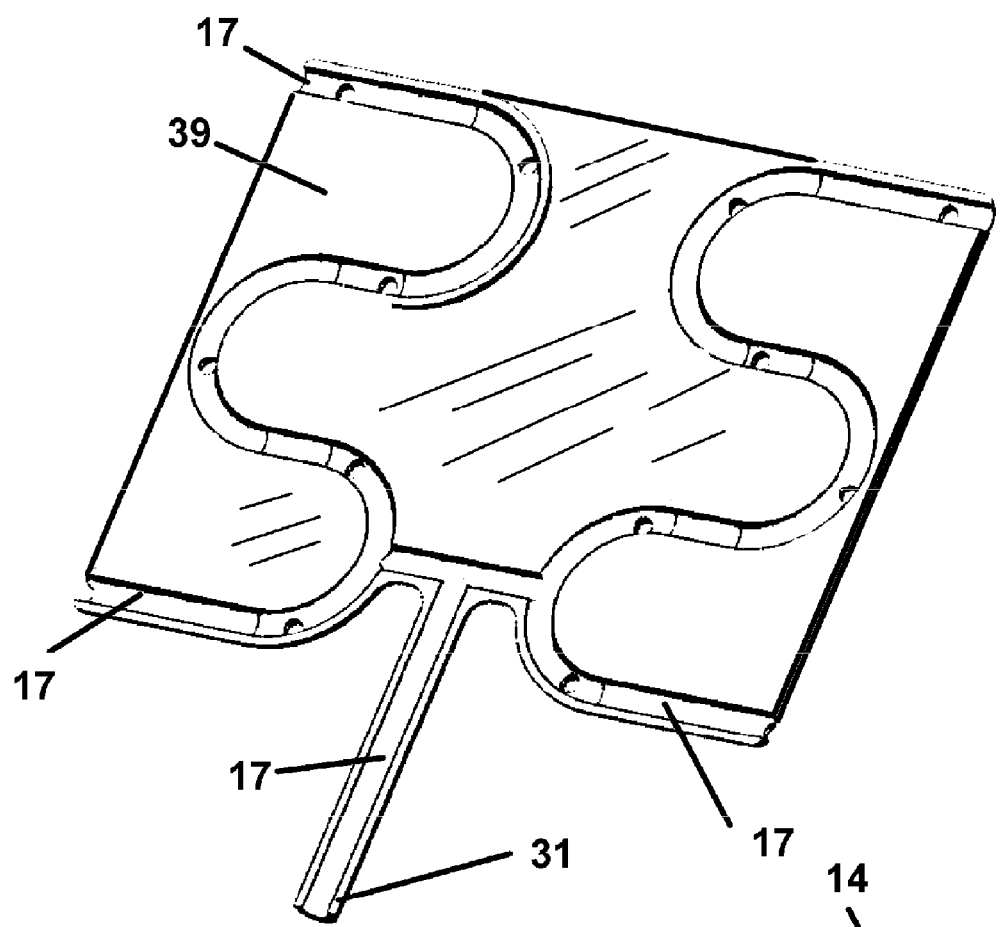
FIG. 5 depicts a half portion of a mode of the device where the conduit is formed by depressions in two planar surfaces which are later joined and the neck portion engages multiple pathways for fluid drainage.
Figure 6:
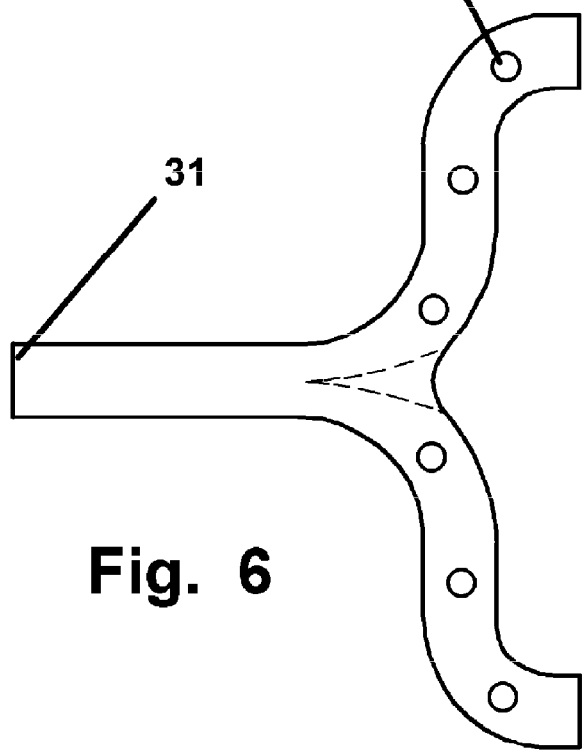
FIG. 6 depicts a mode of the conduit portion of the device adapted at one end for engagement to the shunt or other component, and having a bifurcated flow from two conduits at a second end.

When employing a bifurcated conduit 12 such as in FIGS. 3, 5 and 6, the size of the extensions 40 and 41 in sealed communication with the axial passage 17 of the neck portion 31, can also be adjusted along with the aforementioned adjustments for fluid flow.

In use, with the proper serpentine conduit 12 chosen with desired fluid flow rates, it is mounted to the engagement component 16 which would be implanted to communicate with the anterior chamber 19. The serpentine conduit 12 would be placed within a space 45 within the scleral layer 49 of the eye by formation of a flap 51 underneath which the conduit 12 is placed.

The conduit 12 may be formed from tubular material as in FIG. 1, or from two planar components 39 as in FIG. 5, having ½ of the conduit 12 formed therein. Joining the planar components would form the serpentine conduit 12. This version is especially customizable in that different planar components may be chosen to form the various dimensional characteristics of the conduit 12 desired, and then assembled to the engagement component 16.

Also shown on a number of embodiments are support braces 53 which extend in between or along the sections 13. The braces 53 have been found to better maintain the shape of the device 10 when implanted in the sclera tissue over time.

While all of the fundamental characteristics and features of the present invention have been described herein, with reference to particular embodiments thereof, a latitude of modification, various changes and substitutions are intended in the foregoing disclosure and it will be apparent that in some instance, some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined by the following claims.

What is claimed is:

1. An implantable drain for venting fluid from the anterior chamber of an eye comprising:
    a shunt having a first end and a second end and a passageway therethrough;
    said first end of said shunt adapted to engage within the anterior chamber of an eye;
    a conduit having a sidewall running between a first end and a second end, said conduit having an axial passage running therethrough and communicating with said first end;
    a plurality of apertures communicating through said sidewall with said axial passage;
    means for a removable sealed engagement of said first end of said conduit with said second end of said shunt;
    said sealed engagement connecting said passageway with said axial passage; and
    said conduit adapted for mounting within a space formed in the plane formed by the scleral layer of said eye, whereby fluid from said anterior chamber communicated to said scleral layer when said shunt is engaged with said anterior chamber;
    said conduit having a beginning at said first end of said conduit and to a serpentine shaped portion;
    said serpentine portion formed by a plurality of segments of said conduit traversing back and forth across an axis extending from said first end to said second end of said conduit; said serpentine portion having a plurality of said apertures therein;
    said serpentine portion and said neck portion combining to yield a total aggregate length of said conduit which is longer than a first length of said conduit running along a line directly between said first end and said second end; and
    said aggregate length providing means to place a longer conduit within said sclera within a space in said sclera adapted in a length of said space to house a said conduit of said first length therein.

2. The implantable drain of claim 1 wherein said serpentine portion of said conduit contains sufficient said segments to yield a said aggregate length of said conduit between two and three times said first length.

3. The implantable drain of claim 2 additionally comprising;
    a plurality of said conduits in a group, each having a different respective said aggregate length and each having said apertures running along said respective length;
    each of said plurality of conduits engageable in a sealed engagement with said second end of said shunt;
    whereby means for a varying of a fluid volume evacuated from said anterior chamber is provided through a selecting and engaging any one of said plurality of conduits to said shunt.

4. The implantable drain of claim 3 additionally comprising:
- secondary means for a varying of said fluid volume evacuated, provided by a selecting of one or a combination of, said conduits from said group having having respective larger or smaller diameter said axial passages or larger and smaller said apertures, and
- operatively engaging those selected.

5. The implantable drain of claim 1 additionally comprising;
- a plurality of said conduits in a group, each having a different respective said aggregate length and each having said apertures running along said respective length;
- each of said plurality of conduits engageable in a sealed engagement with said second end of said shunt;
- whereby means for a varying of a fluid volume evacuated from said anterior chamber is provided through a selecting and engaging any one of said plurality of conduits to said shunt.

6. The implantable drain of claim 5 additionally comprising:
- secondary means for a varying of said fluid volume evacuated, provided by a selecting of one or a combination of, said conduits from said group having having respective larger or smaller diameter said axial passages or larger and smaller said apertures, and
- operatively engaging those selected.

* * * * *